United States Patent
Rognin

(10) Patent No.: US 9,192,357 B2
(45) Date of Patent: Nov. 24, 2015

(54) METHOD AND SYSTEM FOR QUANTITATIVE VECTORIAL PERFUSION BASED UPON BLOOD FLOW DIRECTION USING 4D MEDICAL IMAGING

(71) Applicants: KABUSHIKI KAISHA TOSHIBA, Tokyo (JP); TOSHIBA MEDICAL SYSTEMS CORPORATION, Otawara-Shi, Tochigi-Ken (JP)

(72) Inventor: Nicolas Rognin, Bothell, WA (US)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 131 days.

(21) Appl. No.: 13/770,043

(22) Filed: Feb. 19, 2013

(65) Prior Publication Data

US 2014/0236004 A1 Aug. 21, 2014

(51) Int. Cl.
*A61B 8/08* (2006.01)
*A61B 8/06* (2006.01)

(52) U.S. Cl.
CPC ............. *A61B 8/481* (2013.01); *A61B 8/5223* (2013.01); *A61B 8/06* (2013.01); *A61B 8/5207* (2013.01)

(58) Field of Classification Search
CPC .... A61B 8/5223; A61B 8/481; A61B 8/5207; A61B 8/06
See application file for complete search history.

(56) References Cited

U.S. PATENT DOCUMENTS

2008/0194943 A1* 8/2008 Lorenz et al. ................ 600/419

FOREIGN PATENT DOCUMENTS

| WO | 2005/114229 A2 | 12/2005 |
| WO | 2006/067201 A2 | 6/2006 |
| WO | 2012/041822 A2 | 4/2012 |

OTHER PUBLICATIONS

Scott, "Towards a Quantitative Methodology for the Assement of Cerebral Blood Flow in Magnetic Resonance Imaging". thesis, Univeristy of Manchester School of Medicine. 2005.*

* cited by examiner

*Primary Examiner* — Long V Le
*Assistant Examiner* — Colin T Sakamoto
(74) *Attorney, Agent, or Firm* — Yoshida & Associates, LLC

(57) ABSTRACT

A tissue response in a predetermined unit of volume or area tissue of interest is determined by excluding some data of the adjacent tissues based upon a blood flow direction with respect to the tissue of interest. The exclusion is based upon a predetermined time-related parameter such as time-to-peak and mean-transit time in the fitted curves of the uptake of a contrast agent in the adjacent tissues and the tissue of interest. Furthermore, the blood flow direction is determined in terms of a 3D vector based upon a plurality of weighted individual vectors from the adjacent or neighboring voxels with respect to the voxel of interest.

22 Claims, 7 Drawing Sheets

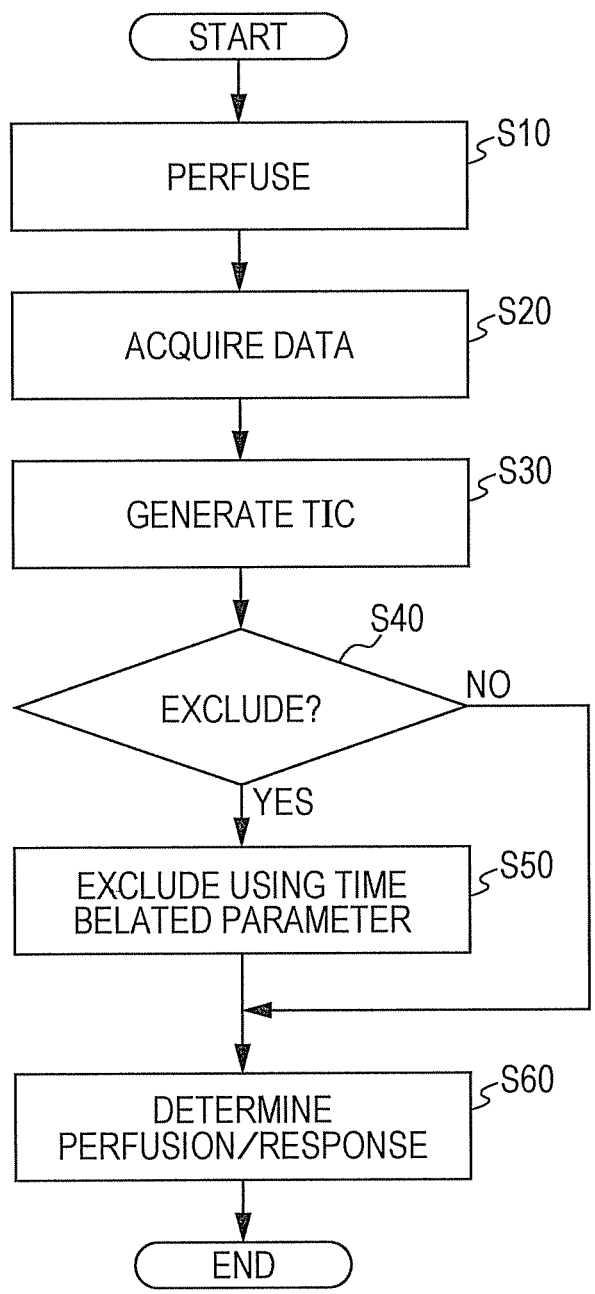

METHOD AND SYSTEM FOR QUANTITATIVE VECTORIAL PERFUSION BASED UPON BLOOD FLOW DIRECTION USING 4D MEDICAL IMAGING

FIELD

Embodiments described herein relate generally to perfusion quantification in ultrasound diagnostic imaging systems and method of performing the same.

BACKGROUND

As illustrated in FIG. 1, a conventional ultrasound imaging system includes a processing unit 1, a display unit 2, a cable 3 and an ultrasound transducer unit or probe 4. The probe or transducer 4 is connected to the processing unit 1 via the cable 3. The processing unit 1 generally controls the transducer unit 4 for transmitting ultrasound pulses towards a region of interest in a patient and receiving the ultrasound echoes reflected from the patient. The processing unit 1 concurrently receives from the transducer unit 4 in real time the reflected ultrasound signals for further processing so as to display on the display unit 2 an image of the region of the interest.

Diagnostic imaging includes the assessment of blood perfusion for several applications and especially in ultrasound analysis. The perfusion assessment is based on the analysis of a sequence of ultrasound contrast images that are obtained after administering an ultrasound contrast agent (UCA) to a patient. One exemplary UCA is suspensions of gas bubbles in a liquid carrier and is referred to as gas-filled microvesicles. Another kind of UCA is suspensions of porous microparticles of polymers or other solids, which carry gas bubbles entrapped within the pores of the microparticles. In general, the contrast agent acts as an efficient ultrasound reflector of ultrasound waves which result in echo-power signal. Since the contrast agent flows substantially at the same velocity as the blood in the patient, its tracking provides information about the perfusion of the blood in a region of interest.

In a typically implemented destruction-replenishment technique, the organ is perfused with the contrast agent such as microbubbles at a constant rate, and the microbubbles are then destroyed by a flash of sufficient acoustic energy in the imaging plane. Quantitative information about the blood perfusion is derived by measuring echo-power signal over time of the replenishment or reperfusion of the microbubbles in a region of interest (ROI). The above measuring technique requires a constant and continuous supply of the contrast agent, called infusion. The continuous administration requires a specific push-syringe pump introducing an additional level complexity in the medical contrast exam. In addition, increase in cost is possible because more than one vial of contrast agent may be necessary. Finally, potential bio-effects may result from the use of a high acoustic energy level in combination with microbubbles.

Another perfusion technique is a bolus that is a single dose of the contrast agent which is provided over a short period of time, typically in the range of 2 to 20 seconds. In comparison to the destruction-replenishment technique, the bolus technique is simpler to control and is less costly. Following bolus intravenous administration in bolus, the contrast uptake in a given organ increases over time (wash-in phase) to reach a maximum value and then gradually decreases (wash-out phase). In general, since the contrast uptake kinetics is spatially varying in the body, the current mathematical modeling techniques known in the art are not necessarily suitable for a rigorous representation of the perfusion process.

Upon focusing in one particular region of interest (ROI), certain mathematical models may be suitable for a rigorous representation of the perfusion process. On the other hand, the blood flow is all inclusive or non-discriminatory in its direction with respect to the ROI.

For the above reasons, it remains desirable to refine the assessment of the perfusion process for a rigorous representation of the perfusion process in a particular ROI.

BRIEF DESCRIPTION OF THE DRAWINGS

FIG. 13 is a flow chart illustrating exemplary steps involved in a process of quantifying tissue perfusion response according to the current invention.

DETAILED DESCRIPTION

Figure 1:
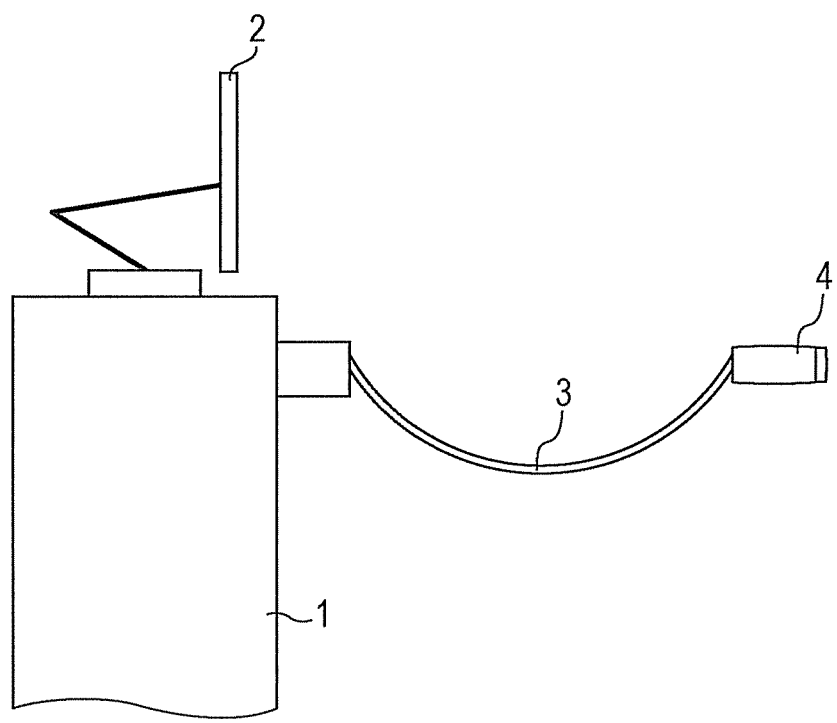
FIG. 1 is a diagram illustrating one exemplary prior art ultrasound imaging system.

Embodiments of the ultrasound imaging system according to the current invention include a probe or transducer unit, a processing unit and an optional cable connecting the probe to the processing unit. In general, the embodiments of the probe include at least some of the structures, components and elements of a conventional ultrasound probe. That is, one embodiment of the probe generates ultrasound pulses and transmits them towards a certain area of a patient. The embodiment also receives the ultrasound echoes reflected from the patient. While many embodiments of the probe are generally hand-held devices, some are not hand-held devices.

According to the current invention, exemplary embodiments of the ultrasound diagnosis apparatus will be explained below in detail with reference to the accompanying drawings. Now referring to FIG. 2, a schematic diagram illustrates a first embodiment of the ultrasound diagnosis apparatus according to the current invention. The first embodiment includes an ultrasound probe 100, a monitor 120, a touch input device 130 and an apparatus main body 1000. One embodiment of the ultrasound probe 100 further includes a plurality of transducer elements such as piezoelectric vibrators, which generate ultrasound based on a driving signal supplied from a transmitting unit 111 housed in the apparatus main body 1000.

As ultrasound is transmitted from the transducer elements such as piezoelectric vibrators in the ultrasound probe 100 to the subject Pt, the transmitted ultrasound is consecutively reflected by discontinuity planes of acoustic impedance in internal body tissue of the subject Pt and is also received as a reflected wave signal by the piezoelectric vibrators of the ultrasound probe 100. The amplitude of the received reflected wave signal depends on a difference in the acoustic impedance of the discontinuity planes that reflect the ultrasound. For example, when a transmitted ultrasound pulse is reflected by a moving blood flow or a surface of a heart wall, a reflected wave signal is affected by a frequency deviation. That is, due to the Doppler effect, the reflected wave signal is dependent on a velocity component in the ultrasound transmitting direction of a moving object.

The apparatus main body 1000 ultimately generates signals representing an ultrasound image. The apparatus main body 1000 controls the transmission of ultrasound from the probe 100 towards a region of interest in a patient as well as the reception of a reflected wave at the ultrasound probe 100. The apparatus main body 1000 includes a transmitting unit 111, a receiving unit 112, a B-mode processing unit 113, a Doppler processing unit 114, a processing unit 115, an image memory 116, a control unit 117 and an internal storage unit 118, all of which are connected via internal bus.

Figure 2:
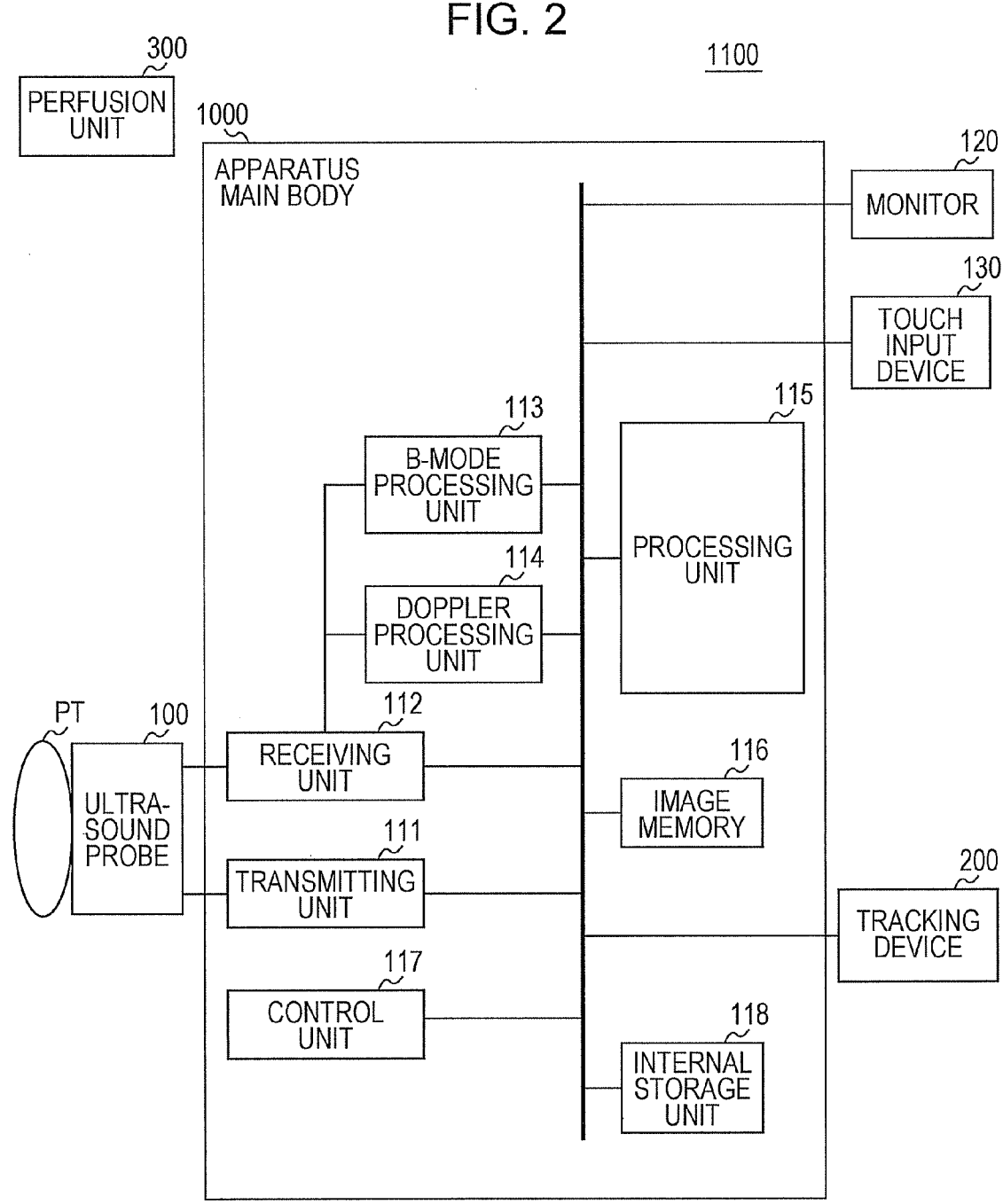
FIG. 2 is a schematic diagram illustrating a first embodiment of the ultrasound diagnosis apparatus according to the current invention.

Still referring to FIG. 2, a system 1100 for determining a tissue perfusion response includes a perfusion unit 300 in addition to the apparatus main body 1000 in one embodiment according to the current invention. In one exemplary implementation, the perfusion unit 300 provides a single dose of a predetermined perfusion contrast agent over a short period of time, typically of the range of approximately 2 to 20 seconds for providing a bolus administration. One exemplary embodiment of the perfusion unit 300 includes a syringe containing a relatively small amount of the predetermined contrast agent.

Accordingly, the probe 100 placed over a region of interest to acquire data after the above described bolus administration of the predetermined perfusion contrast agent. The acquired data is generated from detected echoes reflected from the region of interest to delineate a time sequence of contrast-enhanced ultrasound volumes. The acquired data is stored in a predetermined memory device such as the image memory 116 or the internal storage unit for further processing. In general, a microprocessor such as the processing unit 115 running a predetermined software program processes a time sequence of contrast-enhanced ultrasound volumes to quantify perfusion in biological tissues. A tissue perfusion response per unit volume of interest is estimated to provide quantitative functional parameters such as blood volume and blood flow.

Figure 3:
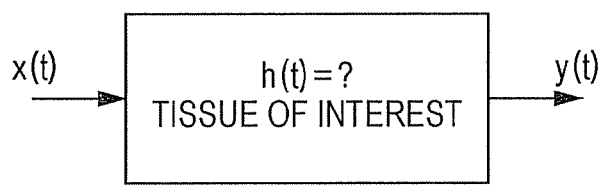
FIG. 3 is a diagram illustrating a system identification approach in perfusion quantification in modalities including computer tomography (CT), positron emission tomography (PET) and magnetic resonance imaging (MRI) according to the current invention.

Now referring to FIG. 3, a diagram illustrates a system identification approach in perfusion quantification in modalities including computer tomography (CT), positron emission tomography (PET) and magnetic resonance imaging (MRI) according to the current invention. A function x(t) is an input function delineating a dynamic uptake of the contrast agent over time t in an artery feeding the tissue region of interest (tROI). A function y(t) is an output function delineating a dynamic uptake of the contrast agent over time t in the tissue region of interest (tROI). Lastly, h(t) is a transfer function to be determined to represent a tissue perfusion response over time t as indicated by a question mark in the tROI. The output function y(t) is defined by the convolution of input function x(t) and the tissue perfusion response h(t) as denoted by $$y(t)=x(t)*h(t).$$

Consequently, the tissue perfusion response h(t) in a tissue region of interest (tROI) is obtained through deconvolution of an input function x(t) and an output function y(t) as denoted by $$h(t)=y(t)*^{-1}x(t).$$

In medical imaging, a certain set of time-intensity curves (TIC) relates to the kinetic of a contrast agent uptake in a region of interest (ROI) which outlines a portion of tissue volume to be analyzed. Perfusion quantification relates to parameters indicative of blood volume or blood flow that is derived from the TICs. Nevertheless, the TIC is not only a function of the tissue perfusion response to be estimated, but also the contrast agent that is intravenously administrated to the patient as a bolus. In a clinical environment, the injection conditions vary from one exam to another due to a type of the contrast agent, its dose and or its injection rate or patient condition (e.g. cardiac output). Because the variations are reflected in the acquired data, the subsequently generated TICs lack consistency that is necessary for reproducing the perfusion quantification.

For the above reasons, to compute a tissue perfusion response independently of injections conditions or parameters, the contrast imaging systems and methods according to the current invention utilize a system identification approach. As shown in FIG. 3, the tissue perfusion response h(t) in a tissue region of interest (tROI) is obtained by deconvolution of an input function x(t) and an output function y(t). The output function y(t) is based upon the measured TIC in the tROI. According to one prior art approach, the input function x(t) is optionally chosen by a clinician by arbitrarily drawing a ROI in an artery that is assumed to feed the ROI. The prior art manual operation is strongly operator-dependent and thus introduces an additional source of variability in perfusion quantification.

One embodiment of the system and the method for quantifying tissue perfusion response according to the current invention utilizes a time-sequence of volumetric data (4D) acquired by a contrast-enhanced ultrasound imaging device. The term, 4D is defined to encompass volumetric time-intensity data that is generated from ultrasound reflected echo data from a region of interest over a predetermined amount of time. Since the volumetric data is generally three-dimensional (3D) and a time sequence is another dimension, the four-dimensional (4D) refers to a time sequence volumetric data. Another embodiment of the system and the method for quantifying tissue perfusion response according to the current invention processes a time-sequence of two-dimensional data acquired by a contrast-enhanced ultrasound imaging device. Yet another embodiment of the system and the method for quantifying tissue perfusion response according to the current invention processes a time-sequence of one-dimensional data acquired by a contrast-enhanced ultrasound imaging device.

The embodiments of the system and the method for quantifying tissue perfusion response according to the current invention substantially remove sources of variability in perfusion quantification such as injection conditions and operator dependency from the definition of the input function. One embodiment of the system and the method for quantifying tissue perfusion response determines a tissue perfusion response per voxel along a predetermined blood flow direction according to the current invention. That is, the embodiment acquires data using a predetermined modality as a function of time and determines a time-related parameter value based upon the acquired data for each of a predetermined set of voxels consisting of adjacent voxels and at least one voxel of interest. Subsequently, the embodiment optionally excludes some data corresponding to any one of the adjacent voxels in the immediate and distant neighborhood of the voxel of interest along a predetermined blood flow direction to the voxel of interest based upon the time-related parameter value. After the exclusion, the remaining acquired data defines selected adjacent voxels. In other words, spatial distribution of contrast agent is considered based upon the interaction between the voxel of interest and its adjacent voxels. Furthermore, the embodiment determines a local input function based the acquired data of the selected adjacent voxels and lastly determines the tissue perfusion response based upon the local input function and an output function according to the acquired data.

The tissue perfusion response is obtained by deconvolution of an input function and an output function, where the output function is the fitted time-intensity curve (TIC) in the voxel of interest and the input function is defined by a selective exclusion of fitted TICs from voxels adjacent to the voxel of interest. The exclusion of the adjacent voxels is based on a predetermined blood flow direction relative to the voxel of interest according to the current invention. Furthermore, the predetermined blood flow direction is not limited to a particular single orientation with respect to the voxel or a group of voxels according to the invention. In other words, the blood flow directions include a combination of a plurality of predetermined blood flow directions with respect to the predetermined volume of the region of interest.

Figure 4:
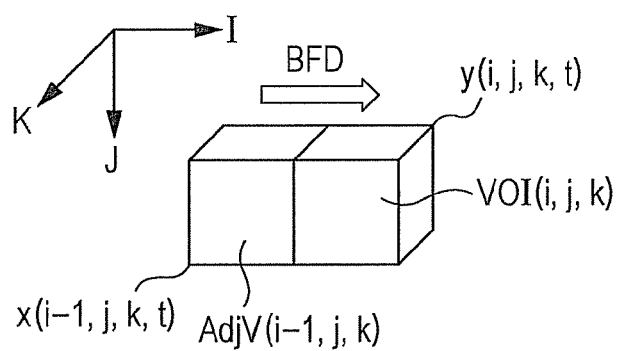
FIG. 4 is a diagram illustrating a predetermined single blood flow direction with respect to a voxel of interest according to current invention.

Now referring to FIG. 4, a diagram illustrates a predetermined single blood flow direction with respect to a region of interest (ROI) according to current invention. For a particular implementation, embodiments of the system and the method for quantifying tissue perfusion response define a unit of the data such as a voxel or a group of voxels according to the current invention. For example, a voxel of interest VOI is located at coordinates (i, j, k) while an adjacent voxel AdjV is located at coordinates (i−1, j, k) in the predetermined set of axes I, J and K as indicated by the arrows. Assuming that the blood flow direction BFD is from the adjacent voxel AdjV to the voxel of interest VOI along the axis I as indicated by an arrow, a tissue perfusion response is determined based upon an input function and an output function in one embodiment of the system and the method according to the current invention. The local input function is an input function delineating a dynamic uptake of the contrast agent over time t in the adjacent voxel AdjV(i−1, j, k) feeding the voxel of interest VOI(i, j, k) in the predetermined single blood flow direction BFD. The local input function is thus defined as x(i−1, j, k, t). The local output function is an output function delineating a dynamic uptake of the contrast agent over time t in the voxel of interest VOI(i, j, k) in receiving blood flow in the predetermined single direction BFD. The local output function is thus defined as y(i, j, k, t). Consequently, the tissue perfusion response h(t) in the voxel of interest VOI is obtained by deconvolution of the local input function x(i−1, j, k, t) and the local output function y(i, j, k, t) as denoted by $$h(t)=y(i,j,k,t)*^{-1}x(i-1,j,k,t).$$

Figure 5:
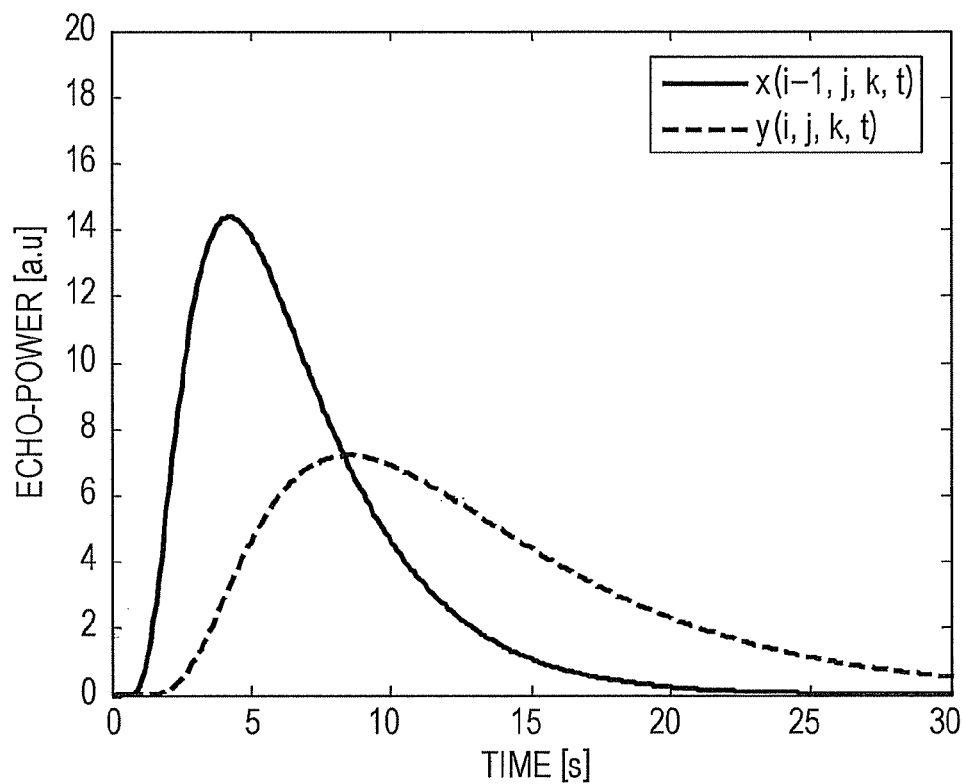
FIG. 5 is a graph illustrating time-intensity curves of a predetermined contrast agent in a predetermined single blood flow direction with respect to a voxel of interest according to current invention.

Now referring to FIG. 5, a graph illustrates time-intensity curves of a predetermined contrast agent in a predetermined single blood flow direction with respect to a region of interest (ROI) according to current invention. The y axis is echo-power (quantity proportional to relative contrast agent concentration) of the detected signal in a predetermined unit while the x axis is time in second. In determining the tissue perfusion response, the local input function x(i−1, j, k, t) and the local output function y(i, j, k, t) are respectively drawn by a slid line and a dotted line. As illustrated in the graph, a peak of the local input function x(i−1, j, k, t) precedes the local output function y(i, j, k, t) in time. Although FIG. 5 illustrates only a single input unction as indicated by the time-intensity curve (TIC), when a plurality of input functions exists, a time-related parameter such as time-to-peak (TTP) is used to exclude some of these input functions. The time-related parameter is not limited to the time-to-peak and includes other time-related parameters such as median transit time, mean transit time or rising time. In addition, the input function is not limited to blood flow along a particular single direction and includes blood flow along a plurality of directions along axes with respect to the region of interest.

Figure 6:
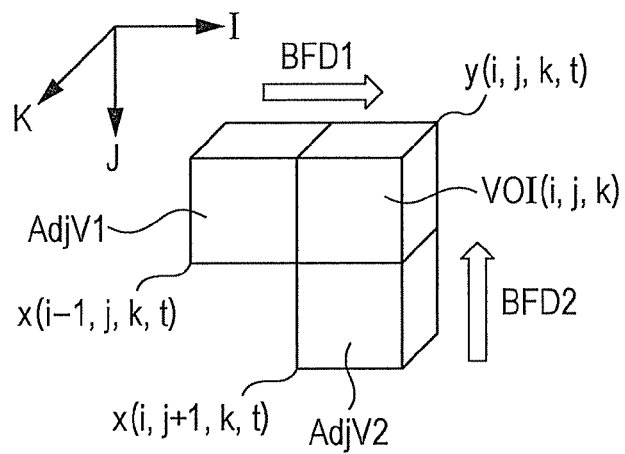
FIG. 6 is a diagram illustrating predetermined two blood flow directions with respect to a voxel of interest according to current invention.

Now referring to FIG. 6, a diagram illustrates predetermined two blood flow directions with respect to a region of interest (ROI) according to current invention. For a particular implementation, embodiments of the system and the method for quantifying tissue perfusion response define a unit of the data such as a voxel according to the current invention. For example, a voxel of interest VOI is located at coordinates (i, j, k) while two adjacent voxels AdjV1 and AdjV2 are respectively located at coordinates (i−1, j, k) and (i, j+1, k) in the predetermined set of axes I, J and K as indicated by the arrows. It is assumed that a first blood flow direction BFD1 is from the adjacent voxel AdjV1 to the voxel of interest VOI along the axis I as indicated by a first arrow. It is also assumed that a second blood flow direction BFD2 is from the adjacent voxel AdjV2 to the voxel of interest VOI along the axis J as indicated by a second arrow.

In this regard, a tissue perfusion response is determined based upon two input functions and an output function in one embodiment of the system and the method according to the current invention. The local input function is an input function delineating a dynamic uptake of the contrast agent over time t in the two adjacent voxels AdjV1(i−1, j, k) and AdjV2 (i, j+1, k) feeding the voxel of interest VOI(i, j, k) in the predetermined two blood flow directions BFD1 and BFD2. Thus, the local input function is defined as a sum of x(i−1, j, k, t) and x(i, j+1, k, t). Alternatively, the local input function is defined as an average of or any combinations of the two definitions. The local output function is an output function delineating a dynamic uptake of the contrast agent over time t in the voxel of interest VOI(i, j, k) in receiving blood flow in the predetermined two directions BFD1 and BFD2. The local output function is thus defined as y(i, j, k, t). Consequently, the tissue perfusion response h(t) in the voxel of interest VOI is obtained by deconvolution of the sum of the local input functions {x(i−1, j, k, t)+x(i, j+1, k, t)} and the local output function y(i, j, k, t) as denoted by $$h(t)=y(i,j,k,t)*^{-1}\{x(i-1,j,k,t)+x(i,j+1,k,t)\}.$$

Figure 7:
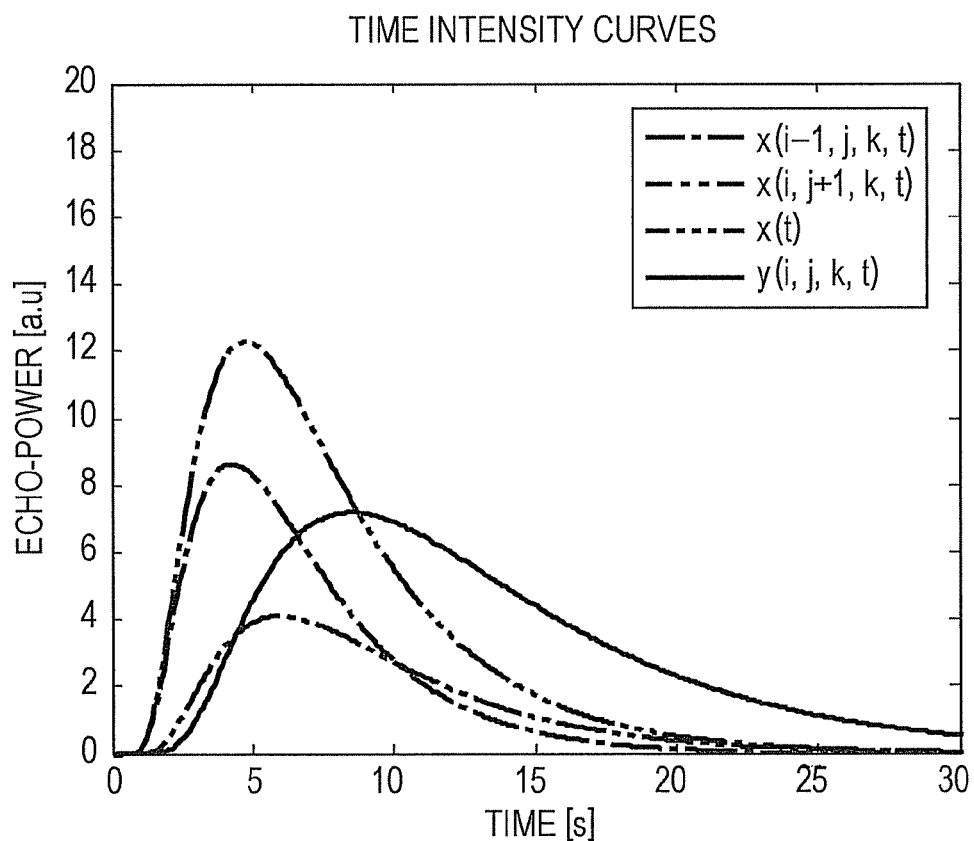
FIG. 7 is a graph illustrating time-intensity curves of a predetermined contrast agent in predetermined two blood flow directions with respect to a voxel of interest according to current invention.

Now referring to FIG. 7, a graph illustrates time-intensity curves of a predetermined contrast agent in predetermined two blood flow directions with respect to a region of interest (ROI) according to current invention. The y axis is echo-power of the detected signal in a predetermined unit while the x axis is time in second. In determining the tissue perfusion response, the first local input function x(i−1, j, k, t), the second local input function x(i, j+1, k, t) and the local output function y(i, j, k, t) are respectively drawn by a single dot line, a double-dotted line and a solid line. The sum of the first local input function x(i−1, j, k, t) and the second local input function x(i, j+1, k, t) is also drawn in the triple-dotted line. As illustrated in the graph, a peak of the first local input function x(i−1, j, k, t) and that of the second local input function x(i, j+1, k, t) both proceed that of the local output function y(i, j, k, t) in time. Although FIG. 7 illustrates only two input functions as indicated by the time-intensity curves (TICs), when more than two input functions exist, a time-related parameter such as time-to-peak (TTP) is used to exclude some of these input functions. The time-related parameter is not limited to the time-to-peak and includes other time-related parameters such as median transit time, mean transit time or rising time. In addition, the input function is not limited to blood flow along particular two directions and includes blood flow along a plurality of directions along axes with respect to the region of interest.

Figure 8:
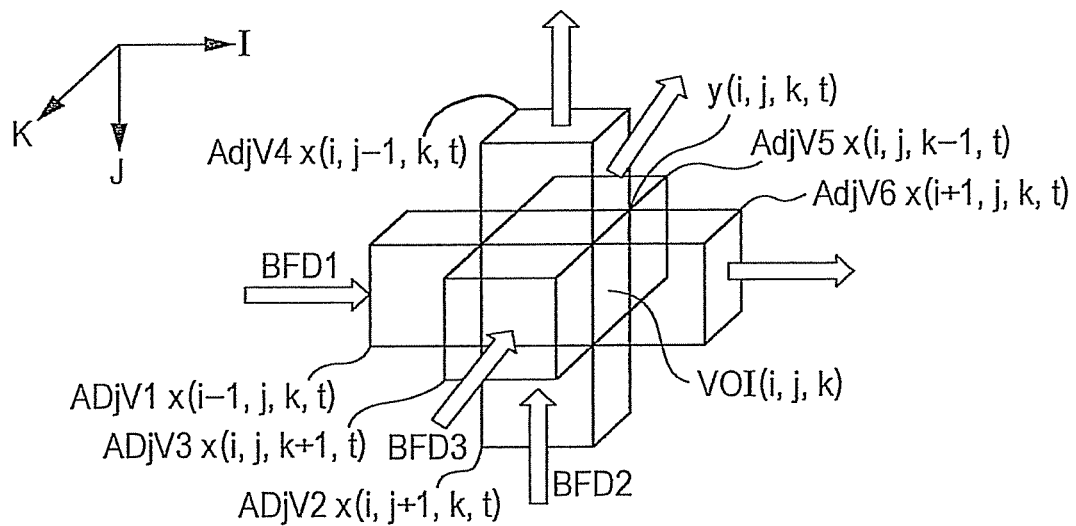
FIG. 8 is a diagram illustrating predetermined six blood flow directions with respect to a voxel of interest according to current invention.

Now referring to FIG. 8, a diagram illustrates predetermined six blood flow directions with respect to a region of interest (ROI) according to current invention. For a particular implementation, embodiments of the system and the method for quantifying tissue perfusion response define a unit of the data such as a voxel according to the current invention. For example, a voxel of interest VOI is located at coordinates (i, j, k) while six adjacent voxels AdjV1 through AdjV6 are respectively located at coordinates (i−1, j, k) (i, j+1, k), (i, j, k+1), (i, j−1, k), (i, j, k−1) and (i+1, j, k) in the predetermined set of axes I, J and K as indicated by the arrows. It is assumed that a first blood flow direction BFD1 is from the adjacent voxel AdjV1 to the voxel of interest VOI along the axis I as indicated by a first arrow. It is also assumed that a second blood flow direction BFD2 is from the adjacent voxel AdjV2 to the voxel of interest VOI along the axis J as indicated by a second arrow. Furthermore, it is assumed that a third blood flow direction BFD3 is from the adjacent voxel Adj3 to the voxel of interest VOI along the axis K as indicated by a second arrow. By the same token, fourth through sixth blood flow directions BFD4 through BFD6 are respectively from the adjacent voxel AdjV4 through AdjV6 to the voxel of interest VOI along a predetermined axis as indicated by a corresponding arrow.

In this regard, a tissue perfusion response is determined based upon three input functions and an output function in one embodiment of the system and the method according to the current invention. The local input function is an input function delineating a dynamic uptake of the contrast agent over time t in the three adjacent voxels AdjV1 (i−1, j, k), AdjV2(i, j+1, k) and AdjV3(i, j, k+1) feeding the voxel of interest VOI(i, j, k) in the predetermined two blood flow directions BFD1, BFD2 and BFD3. Thus, the local input function is defined as a sum of x(i−1, j, k, t), x(i, j+1, k, t) and x(i, j, k+1, t). The local output function is an output function delineating a dynamic uptake of the contrast agent over time t in the voxel of interest VOI(i, j, k) in receiving blood flow in the predetermined three directions BFD1, BFD2 and BFD3. The local output function is thus defined as y(i, j, k, t). Consequently, the tissue perfusion response h(t) in the voxel of interest VOI is obtained by deconvolution of the sum of the local input functions {x(i−1, j, k, t)+x(i, j+1, k, t)+x(i, j, k+1, t)} and the local output function y(i, j, k, t) as denoted by $$h(t)=y(i,j,k,t)^{*-1}\{x(i-1,j,k,t)+x(i,j+1,k,t)+x(i,j,k+1,t)\}.$$

Figure 9:
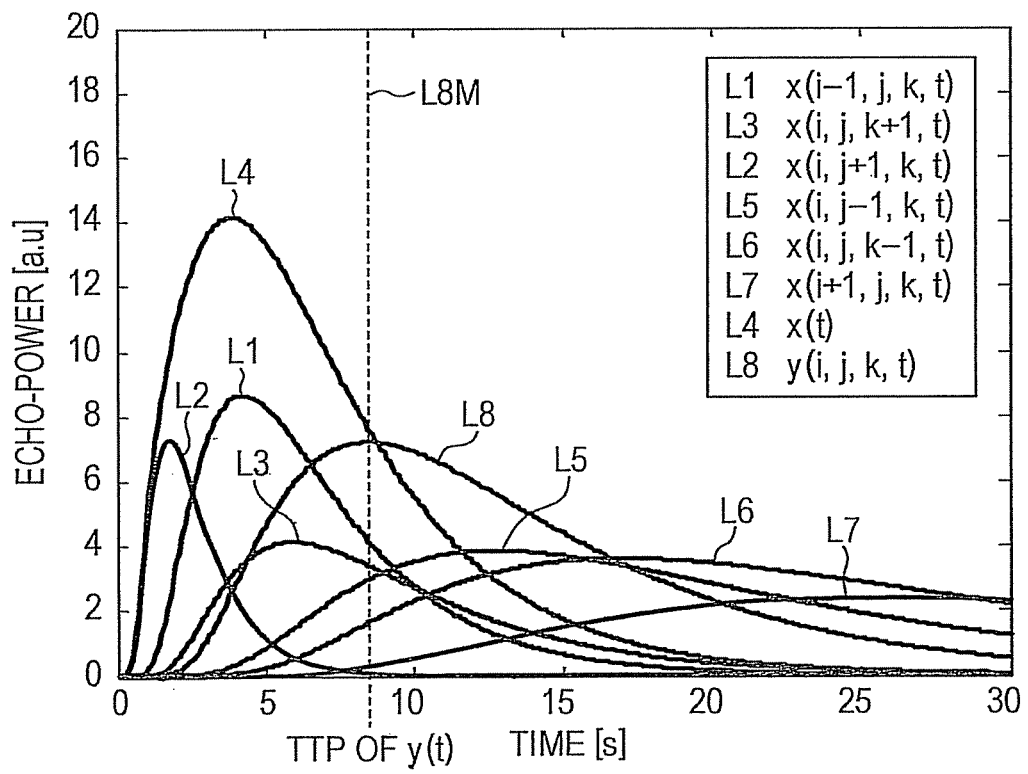
FIG. 9 is a graph illustrating time-intensity curves of a predetermined contrast agent in predetermined six blood flow directions with respect to a voxel of interest according to current invention.

Now referring to FIG. 9, a graph illustrates time-intensity curves of a predetermined contrast agent in predetermined six blood flow directions with respect to a region of interest (ROI) according to current invention. The y axis is echo-power of the detected signal in a predetermined unit while the x axis is time in second. In determining the tissue perfusion response, the first local input function x(i−1, j, k, t), the second local input function x(i, j+1, k, t), the third local input function x(i, j, k+1, t) and the local output function y(i, j, k, t) are respectively drawn by a first line L1, a second line L2 and a third line L3. The sum of the first local input function x(i−1, j, k, t), the second local input function x(i, j+1, k, t) and the third local input function x(i, j, k+1, t) is also drawn in a fourth line L4. As illustrated in the graph, a peak of the first local input function x(i−1, j, k, t), the second local input function x(i, j+1, k, t) and the third local input function x(i, j, k+1, t) all proceed that of the local output function y(i, j, k, t) in time. Although FIG. 9 illustrates six input functions as indicated by the time-intensity curves (TICs) of lines L1 through L3 and L5 and L7, a time-related parameter such as time-to-peak (TTP) is used to exclude three of these input functions whose TICs are drawn by the lines L5 and L7.

The optional exclusion is critical in the embodiment of processing data associated with multiple blood flow directions with respect to the voxel of interest VOI(i, j, k). Because the peaks of the TICs as drawn by the lines L5, L6 and L7 lag behind a peak L8M of the output function y(i, j, k, t) at VOI(i, j, k) as drawn by the line L8, the uptake did not take place prior to that in the VOI(i, j, k) along these blood flow directions. That is, the excluded input functions are not in the same blood flow directions with respect to the voxel of interest VOI(i, j, k) so that the uptake as depicted by TICs (L5, L6 and L7) are taking place after the TICs (L1, L2, L3) in time. In other words, any adjacent voxel showing a flow direction out of the voxel of interest is (VOI) is excluded based the rule below in the one embodiment of the system and the method according to the current invention. The remaining adjacent voxels are then selected as adjacent voxels in determining an input function.

if (dT>0) then exclude the adjacent voxel Vn else do not exclude Vn.

where dT=T(Vn)−T(Vi) with

T(Vn): a first time-related parameter value in an adjacent voxel Vn

T(Vi): a second time-related parameter value in voxel of interest VOI

In another embodiment of the system and the method according to the current invention, any adjacent voxel showing a blood flow direction into the voxel of interest is (VOI) is not excluded based an opposite rule below. The remaining adjacent voxels are then selected as adjacent voxels in determining an input function.

if (dT<0) then do not exclude Vn else exclude Vn.

where dT=T(Vn)−T(Vi) with

T(Vn): a first time-related parameter value in adjacent voxel Vn

T(Vi): a second time-related parameter value in voxel of interest VOI

In summary, the above exclusion rule for adjacent voxels is based on a blood flow direction that is exclusively into or out of the voxel of interest. In another embodiment of the invention, the local output function y(i, j, k, t) in time is defined as the combination of fitted TIC from excluded voxels.

Now referring to FIG. 10, in an embodiment of the system and the method according to the current invention, a 3D blood inflow vector $F_{in\_VOI}$ is attributed to the voxel of interest (VOI) and is optionally determined as a linear combination of the selected adjacent voxels as follows $$\overrightarrow{F_{in\_VOI}} = w_1 \overrightarrow{F_{in\_V1}} + w_2 \overrightarrow{F_{in\_V2}}$$

where $F_{in\_V1}$ and $F_{in\_V2}$ are respectively inflow vectors of a first adjacent voxel AdjV1, whose center is located at (r1, θ1, φ1) and a second adjacent voxel AdjV2, whose center is located at (r2, θ2, φ2) in a spherical coordinate system (r, θ, φ) with the 3D center of the VOI as origin. Because of the vectors, the method and the system related to the diagram as illustrated in FIG. 10 is considered as a vectorial perfusion processing scheme. $w_1$ is a first weighing coefficient that is defined as a normalized parameter that is derived from the fitted TIC in the first adjacent voxel AdjV1 while $w_2$ is a second weighing coefficient that is defined as a normalized parameter that is derived from the fitted TIC in the second adjacent voxel AdjV2. Similarly, a set of $F_{in\_V}$ and a corresponding weighing coefficient is provided up to N, defined as below:

$$\overrightarrow{F_{in\_VOI}} = \sum_{i=0}^{N} w_i \overrightarrow{F_{in\_Vi}}$$

In one implementation, the weighing coefficient is an amplitude-related value such as the normalized Area Under the Curve (AUC) with weighing coefficient defined as:

$$w_i = \frac{AUC_i}{\sum_{j=0}^{N} AUC_j}$$

where N is a total number of selected voxels as inflow and j is a selected inflow voxel index.

In other implementation, a weighing coefficient is optionally any parameter that is derived from the tissue response h(t) from the deconvolution process as described above. For example, the normalized AUC of the tissue response (AUC_h) corresponds to the local blood volume (BV), giving the weighting coefficient:

$$w_i = \frac{BV_i}{\sum_{j=0}^{N} BV_j}$$

where $BV_i = AUC_{hi}$. In a second example, a weighting coefficient is the normalized inversed mean transit time (1/MTT_h) that is derived from the tissue response, corresponding to the local blood velocity (BVec), giving the weighting coefficient:

$$w_i = \frac{BVec_i}{\sum_{j=0}^{N} BVec_j}$$

where $$BVec_i = \frac{1}{MTT_{hi}}$$

In a third example, a weighting coefficient is the normalized product of BV and BVec, corresponding to the local blood flow (BF) and defined as $$w_i = \frac{BF_i}{\sum_{j=0}^{N} BF_j}$$

where $$BF_i = BV_i \cdot BVec_i = \frac{AUC_{hi}}{MTT_{hi}}$$

In a fourth example, a weighting coefficient includes adjacent voxels not only in the immediate neighborhood but also at farther distances with respect to the VOI. The immediate neighborhood means that the voxels are directly connected to the voxel of interest at least by one point.

Figure 10:
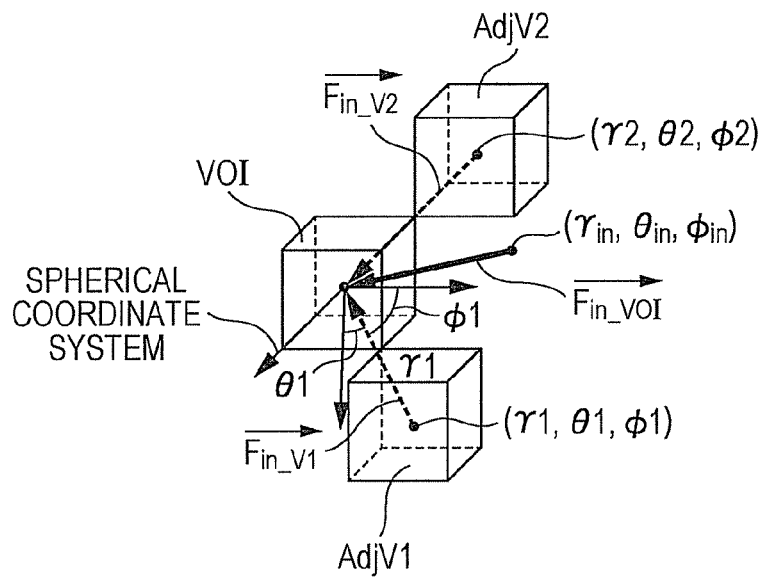
FIG. 10 is a diagram illustrating the 3D inflow vector with respect to a voxel of interest according to current invention.
Figure 11:
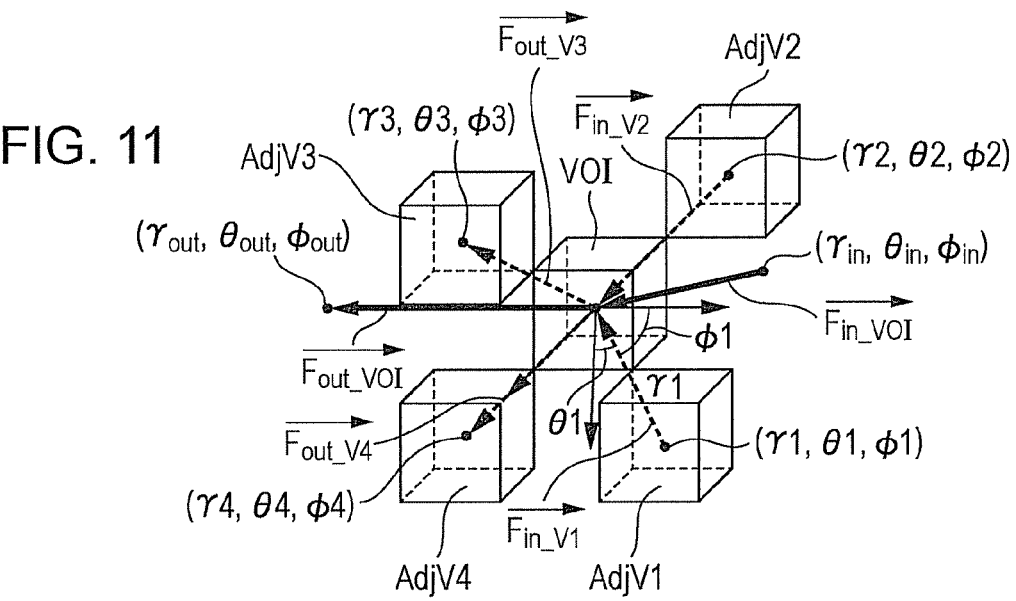
FIG. 11 is a diagram illustrating the 3D inflow and outflow vectors with respect to a voxel of interest according to current invention.

Now referring to FIG. 11, in an embodiment of the system and the method according to the current invention, a 3D blood outflow vector $F_{out\_VOI}$ is attributed to the voxel interest (VOI) in combination to a 3D blood inflow vector $F_{in\_VOI}$, which was described with respect to FIG. 10. Because of the vectors, the method and the system related to the diagram as illustrated in FIG. 10 is considered as a vectorial perfusion processing scheme. A 3D blood inflow vector $F_{in\_VOI}$ is attributed to the voxel of interest (VOI) and is optionally determined as a linear combination of the selected adjacent voxels as follows $$\overrightarrow{F_{in\_VOI}} = w_{1in} \overrightarrow{F_{in\_V1}} + w_{2in} \overrightarrow{F_{in\_V2}}$$

where $\overrightarrow{F_{in\_V1}}$ and $\overrightarrow{F_{in\_V2}}$ are respectively inflow vectors of a first adjacent voxel AdjV1, whose center is located at (r1, θ1, φ1) and a second adjacent voxel AdjV2, whose center is located at (r2, θ2, φ2) in a spherical coordinate system (r, θ, φ) with the 3D center of the VOI as origin. $w_{1in}$ is a first weighing coefficient that is defined as a normalized parameter that is derived from the fitted TIC in the first adjacent voxel AdjV1 while $w_{2in}$ is a second weighing coefficient that is defined as a normalized parameter that is derived from the fitted TIC in the second adjacent voxel AdjV2.

Still referring to FIG. 11, a 3D blood outflow vector, $F_{out\_VOI}$ is attributed to the voxel of interest (VOI) and is optionally determined as a linear combination of the selected adjacent voxels as follows $$\overrightarrow{F_{out\_VOI}} = w_{1out} \overrightarrow{F_{out\_V3}} + w_{2out} \overrightarrow{F_{out\_V4}}$$

where $\overrightarrow{F_{out\_V3}}$ and $\overrightarrow{F_{out\_V4}}$ are respectively outflow vectors of a third adjacent voxel AdjV3, whose center is located at (r3, θ3, φ3) and a fourth adjacent voxel AdjV4, whose center is located at (r4, θ4, φ4) in a spherical coordinate system (r, θ, φ) with the 3D center of the VOI as origin. $w_{1out}$ is a first weighing coefficient that is defined as a normalized parameter that is derived from the fitted TIC in the first adjacent voxel AdjV3 while $w_{2out}$ is a second weighing coefficient that is defined as a normalized parameter that is derived from the fitted TIC in the second adjacent voxel AdjV4. Although only two vectors are illustrated for both the inflow and outflow vector components, either flow is not limited to a pair of vector components and includes a set of $\overrightarrow{F_{in}}$ vector components and a corresponding weighing coefficient $w_i$ is provided up to N as defined below:

$$\vec{F}_{voi} = \sum_{i=0}^{N} w_i \overrightarrow{F_{in}}$$

By the same token, in one implementation, the weighing coefficient is an amplitude-related value such as the normalized AUC with weighing coefficient as defined above. In other implementation, a weighing coefficient is optionally any parameter that is derived from the tissue response h(t) from the deconvolution process as described above.

Furthermore, a field of 3D blood vectors is optionally rendered in colors using the tissue response in a certain implementation. For example, the absolute blood volume (BV), blood velocity (BVec), blood flow (BF) or any other parameters is color coded using the tissue response in one implementation. The time-related parameter is not limited to the time-to-peak and includes median transit time and mean transit time. In addition, the input function is not limited to blood inflow along particular three directions and includes blood flow along a plurality of directions along axes with respect to the region of interest. In another embodiment of the invention, a 3D field vector combining inflow and outflow data is rendered. For example, inflow and outflow are respectively attributed to one primary color such as red and to a second primary color such as blue. In addition, each color gradation follows a predetermined law such as a linear or logarithmic law in luminance as function of the value of the chosen parameter such as BF.

Figure 12:
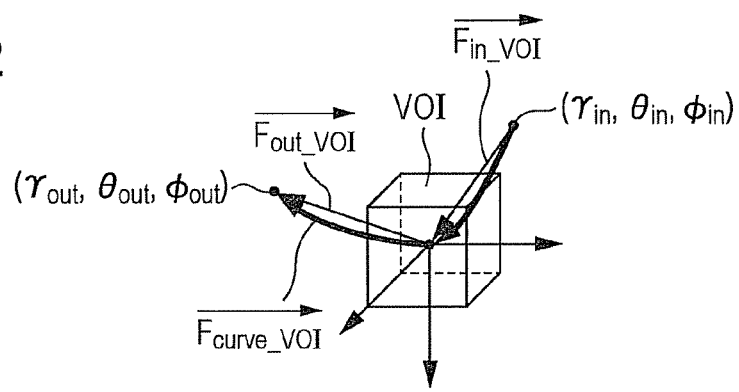
FIG. 12 is a diagram illustrating the computation of a 3D curved vector based on the inflow and outflow vectors with respect to a voxel of interest according to current invention.

Now referring to FIG. 12, the inflow and outflow vectors are used in extrapolation to generate a 3D curved vector with respect to a predetermined VOI in yet another embodiment according to the current invention. The extrapolation process includes Bezier curve and spline, and the generated 3D curved vector represents the curvature of the flow between the inflow and the outflow. In the illustrated example, a 3D inflow vector $\overrightarrow{F_{in\_VOI}}$ and a 3D outflow vector $\overrightarrow{F_{out\_VOI}}$ are extrapolated to generate a 3D blood flow curved vector a 3D inflow vector $\overrightarrow{F_{curved\_VOI}}$ with respect to the voxel of interest (VOI).

In one embodiment of the invention, a statistical parameter such as mean, standard deviation or entropy is derived from 3D field vectors or 3D curved vectors in the volume of interest that contains a group of voxels. The statistical parameter is indicative of the microvasculature state of a certain tissue such as a tumor. For example, the statistical parameter indicates the level of spatial heterogeneity or homogeneity of a portion of the tissue that is manually or automatically delineated by the volume of interest. In this regard, one possible clinical application is that a drug treatment is monitored by the level of spatial heterogeneity of the tumor which is indicative of a patient response to the drug treatment. Patient response is generally positive if the spatial heterogeneity of the tumor decreases. Conversely, patient response is rather negative if the spatial heterogeneity increases. The statistical parametric analysis is applicable to any of the parameters such as BV, BVec and BF that are derived from the tissue response, which is indicative of the perfusion status in a volume of interest. A linear combination of any spatial and perfusion parameters is also optionally used to represent the tissue microvasculature state in other implementations in the embodiments according to the current invention.

The parameters are determined and used in various manners. In one embodiment, a statistical parameter is transformed from 3D field vectors or curved vectors in an irregular grid or a network of connectivity indicative of the microvasculature network or perfusion network, which is laid locally or over a 3D tissue of interest or an entire organ. The networks are optionally the object of advanced statistical analyses to derive a single parameter representative of the perfusion state. In another embodiment, 3D field vectors, curved vectors or tissue response perfusion parameters are used to automatically segment or delineate a 3D tissue of interest such as lesions, tumors, necrotic areas and healthy tissue. In one embodiment, all of the methods and systems described in the present invention are used to quantify and asses the level of binding of a targeted contrast agent in Medical Molecular Imaging. In another embodiment, all of the methods and systems described in the present invention are used to monitor, control or trigger the release of active pharmaceutical ingredients, carried by targeted contrast agents, by a Drug Delivery System mediated by 3D ultrasound or any other medical imaging techniques. Lastly, in one embodiment using artificial intelligence techniques, all of the parameters or set of the selected parameters of the present invention are inputted in a feature vector for training Computer-Aided-Diagnosis (CAD) application software.

In FIGS. 4, 6, 8 10, 11 and 12, although the examples illustrate adjacent voxels as voxels that are immediately adjacent and juxtaposed to the voxel of interest, the embodiments do not necessarily require immediate adjacent voxels to practice the current invention. For this reason, the term, adjacent voxels are interchangeably used in the specification and the claims to include both immediately adjacent voxels that are juxtaposed to the voxel of interest as well as neighboring voxels that are not juxtaposed to the voxel of interest. In this regard, the immediately adjacent voxels as illustrated in FIGS. 10, 11 and 12 include any spatially connected voxels (6 faces+8 corners=14 adjacent voxels) with respect to the voxel of interest. In this regard, a number of immediately juxtaposed voxels ranges from a minimum of 1 to a maximum of 13 with respect to a single voxel of interest. In the context of a pure perfusion process where microbubbles are used in an intravascular or blood-pool contrast agent, the above minimum/maximum selection must be strictly respected according the "law of conservation of energy." That is, no blood inflow/outflow is created or destroyed. One possible exception to this rule is medical molecular imaging where the contrast agent can accumulate in the tissue due to the active process.

Now referring to FIG. 13, a flow chart illustrates exemplary steps involved in a process of quantifying tissue perfusion response according to the current invention. The steps are merely exemplary and optionally include more or less steps or acts in order to practice the invention in other embodiments of the process of quantifying tissue perfusion response according to the current invention. In the illustrated process, the steps are optionally performed by any combination of software and hardware as previously described in the embodiments for quantifying tissue perfusion response according to the current invention. On the other hand, the steps of the illustrated process may be also performed by a certain combination of software and hardware for modalities that have not been previously described, including computer tomography (CT), positron emission tomography (PET), magnetic resonance imaging (MRI) and photoacoustics imaging (PI).

Still referring to FIG. 13, the illustrated process acquires data in a step S20 after a predetermined contrast agent is perfused into a subject in a step S10. The perfusion process allows a predetermined contrast agent such as microbubbles to enter into a region of interest such as a certain tissue volume via blood circulation. The uptake kinetic of the contrast agent is further studied by generating time-intensity curves (TICs) based upon the acquired data in a step S30. One group of the TICs is an input function and is generated according to at least one predetermined blood flow direction with respect to the region of interest. The input function delineates a dynamic uptake of the contrast agent over time t in an artery feeding the tissue region of interest (tROI). In one exemplary implementation, the predetermined directions are parallel to the axes of the coordinate system and selected voxels are adjacent to the voxel(s) of interest in the tissue. The selection of an adjacent voxel is performed according to its blood flow direction with respect to the voxel of interest (VOI) by excluding certain voxels in the neighborhood of the VOI. The other group of the TICs is an output function that delineates a dynamic uptake of the contrast agent over time t in the tROI based upon the voxels.

In the step S30, for generating the TICs, a predetermined blood flow direction includes a blood inflow direction and a blood outflow direction with respect to a certain voxel of interest according to the current invention. In certain embodiments, the blood inflow direction and the blood outflow direction are each a combination of 3D vectors. For example, the blood inflow direction is a combination of two or more of 3D vectors each indicating direction and magnitude of the blood flow that contributes to the blood inflow to the voxel of interest. Similarly, the blood outflow direction is a combination of two or more of 3D vectors each indicating direction and magnitude of the blood flow that contributes to the blood outflow from the voxel of interest. For both of the blood inflow and outflow, the amplitude of the blood flow includes blood volume and flow rate. Furthermore, the 3D vectors are optionally weighed by a set of corresponding weighting coefficients so that a sum of the 3D vectors becomes a blood inflow vector or a blood outflow vector.

In a step S40, it is confirmed whether or not certain TICs are to be excluded from further determination of the tissue perfusion response h(t) in the tROI. The choice is optionally made in advance of the process or during the process according to the current invention. If it is confirmed in the step S40 that the exclusion of the TIC takes place, the process proceeds to a step S50. On the other hand, if it is confirmed in the step S40 that the exclusion of the TIC does not take place, the process proceeds to a step S60.

The exclusion step S50 is performed according to a predetermined exclusion rule so as to exclude some components of the input function that has been generated for more than one predetermined blood flow direction with respect to the region of interest. The predetermined exclusion rule is based upon a time-related parameter or index such as time-to-peak, median transit time, or mean transit time of the time-intensity curves. Another time-related index includes blood flow that is obtained by dividing blood volume by mean transit time. For example, the time-to-peak (TTP) of a first TIC for a first predetermined blood flow direction is longer than that of the output function in a voxel of interest (VOI) while the TTP of a second TIC for a second predetermined blood flow direction is shorter than that of the output function in the VOI. In one exemplary exclusion step S50, either one of the first and second TICs is excluded depending upon the predetermined rule. That is, if the contrast agent uptake is to be studied with respect to the blood flow into the VOI, the second TIC is excluded. On the other hand, if the contrast agent uptake is to be studied with respect to the blood flow out of the VOI, the first TIC is excluded. Since the input function delineates a dynamic uptake of the contrast agent over time t in an artery feeding the tissue region of interest (tROI), the excluded components do not contribute to the uptake of the contrast agent over time t in the artery feeding the tROI under certain situation. Under certain other situations, some components are excluded even if the excluded components contribute to the uptake of the contrast agent over time t in the artery feeding the tROI.

A time-related parameter, a combination of time-related parameters or a combination of time-related parameters and amplitude-related parameters is determined from the fitted curve in any adjacent voxel. Optionally, the above parameters are determined based upon the derivative functions (analytical or numerical) of the fitted curve. For instance, the first derivative function is indicative of blood velocity with respect to time while the second derivative is indicative of blood acceleration. Furthermore, the third derivative is indicative of blood jerk (acceleration change rate) while the fourth derivative function is indicative of blood jounce, and so on for higher derivative functions.

Lastly in a step S60, a tissue perfusion response is determined based upon the above described input and output function. A tissue perfusion response h(t) is a transfer function over time t in the tROI. The output function y(t) is defined by convolving the input function x(t) and the tissue perfusion response h(t) as denoted by $$y(t)=x(t)*h(t).$$

Consequently, the tissue perfusion response h(t) in a tissue region of interest (tROI) is obtained through deconvolution of an input function x(t) and an output function y(t) as denoted by $$h(t)=y(t)*^{-1}x(t).$$

As described above, the input function x(t) is a sum of remaining input function components after the exclusion in the step S50 if the exclusion is confirmed in the step S40. The input function x(t) is also a single predetermined function along a predetermined blood flow direction or optionally a sum of certain specified input function components when exclusion in the step S50 is not confirmed in the step S40.

The above described method and system have substantially improved the quantification of perfusion based upon a combination of the independent contrast agent administration and the exclusion of certain TIC data due to the selected blood flow directions with respect to the volume of interest. This method allows quantifying perfusion in an objective manner because it is independent of contrast agent administration parameters and patient condition such as cardiac output. As described above, the contrast agent is administered into a subject via a bolus administration. That is, the contrast agent administration technique is not limited to a particular dose and or rate in order to determine a tissue perfusion response per voxel of interest in a system and a method according to the current invention.

The above described embodiment is merely illustrative and other implementations of the current inventions are available in both software and hardware. In other words, a system for determining a tissue perfusion response according to the current invention is not limited to a particular set of hardware devices or software programs. In this regard, the system and the method is not limited to a particular modality and also include contrast imaging modalities such as CT, MRI, PET and PI to practice the current invention.

The above process merely describes an exemplary process and is not limited to a particular implementation such as in a number of the cross-point switches and or the adders to practice the current invention. By the same token, the above steps merely illustrate one exemplary implementation and are not limited to a particular number of output sets from the cross-point switches to practice the current invention.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope of the inventions.

What is claimed is:

1. A method of determining a tissue perfusion response, comprising:
    acquiring data comprising voxels using an imaging device in a predetermined modality as a function of time;
    determining a time-related parameter value comprising a time-to-peak parameter value for each of a predetermined set of the voxels consisting of adjacent voxels and at least one voxel of interest in the acquired data;
    excluding based upon the time-related parameter value any one of the adjacent voxels along a predetermined blood flow direction to the voxel of interest, the remaining acquired data defining selected adjacent voxels, wherein any one of the adjacent voxels is excluded if the time-to-peak parameter value of the adjacent voxel exceeds the time-to-peak parameter value of the voxel of interest;
    determining a local input function based the acquired data of the selected adjacent voxels; and
    determining the tissue perfusion response based upon the local input function and an output function according to the acquired data.

2. The method of determining a tissue perfusion response according to claim 1 further comprising applying a predetermined curve fitting technique to the acquired data to obtain a plurality of fitted curves for each of the voxels along at least one predetermined direction with respect to the voxel of interest, wherein the plurality of fitted curves for the adjacent voxels is selected.

3. The method of determining a tissue perfusion response according to claim 1 wherein the tissue perfusion response is determined by deconvolution of the local input function and the output function.

4. The method of determining a tissue perfusion response according to claim 1 wherein the predetermined direction includes a combination of a 3D blood inflow vector and a 3D blood outflow vector with respect the voxel of interest.

5. The method of determining a tissue perfusion response according to claim 4 wherein the 3D blood inflow vector and the 3D blood outflow vector are respectively determined by a set of 3D vectors indicative of blood inflow and a set of 3D vectors indicative of blood outflow from adjacent voxels with respect the voxel of interest.

6. A method of determining a tissue perfusion response using ultrasound, comprising:
    acquiring data comprising voxels and using contrast ultrasound;
    applying a predetermined curve fitting technique to the acquired data to obtain a plurality of fitted curves for a predetermined set of the voxels consisting of adjacent voxels and at least one voxel of interest in the acquired data;
    determining a time-to-peak parameter value based upon the fitted curves for each of the voxels;
    excluding any one of the fitted curves corresponding to the adjacent voxel along a predetermined direction to the voxel of interest if the time-to-peak parameter value of the adjacent voxel exceeds the time-to-peak parameter value of the voxel of interest to define selected adjacent voxels based upon remaining ones of the fitted curves;
    determining a local input function by adding the fitted curves from the selected adjacent voxels; and
    determining the tissue perfusion response based upon the local input function and an output function according to the acquired data.

7. The method of determining a tissue perfusion response according to claim 6 wherein the plurality of fitted curves for the adjacent voxels along at least one predetermined direction with respect to the voxel of interest is selected.

8. The method of determining a tissue perfusion response according to claim 6 wherein the output function is based upon the voxel of interest.

9. The method of determining a tissue perfusion response according to claim 6 wherein the output function is based upon a combination of the voxel of interest and excluded ones of the adjacent voxels.

10. The method of determining a tissue perfusion response according to claim 6 wherein the predetermined direction includes a combination of a 3D blood inflow vector and a 3D blood outflow vector with respect the voxel of interest.

11. A system for determining a tissue perfusion response, comprising:
    a imaging device for acquiring data comprising voxels using a predetermined modality as a function of time; and
    a microprocessor connected to said imaging device for determining a time-related parameter value comprising a time-to-peak parameter value for each of a predetermined set of the voxels consisting of adjacent voxels and at least one voxel of interest in the acquired data, said microprocessor excluding based upon the time-related parameter value any one of the adjacent voxels along a predetermined blood flow direction to the voxel of interest to define selected adjacent voxels, wherein any one of the adjacent voxels is excluded if the time-to-peak parameter value of the adjacent voxel exceeds the time-to-peak parameter value of the voxel of interest, said microprocessor determining a local input function based the acquired data of the selected adjacent voxels, said microprocessor determining the tissue perfusion response based upon the local input function and an output function according to the acquired data.

12. The system for determining a tissue perfusion response according to claim 11 wherein said microprocessor applies a predetermined curve fitting technique to the acquired data to obtain a plurality of fitted curves for each of the voxels along at least one predetermined direction with respect to the voxel of interest, the plurality of fitted curves for the adjacent voxels being selected.

13. The system for determining a tissue perfusion response according to claim 11 wherein the tissue perfusion response is determined by deconvolution of the local input function and the output function.

14. The system for determining a tissue perfusion response according to claim 11 wherein a 3D orientation angle of blood flow into the voxel of interest from the adjacent voxels is determined by a predetermined set of weighing coefficients.

15. The system for determining a tissue perfusion response according to claim 11 wherein the predetermined direction includes a combination of a 3D blood inflow vector and a 3D blood outflow vector with respect the voxel of interest.

16. The system for determining a tissue perfusion response according to claim 15 wherein the 3D blood inflow vector and the 3D blood outflow vector are respectively determined by a set of 3D vectors indicative of blood inflow and a set of 3D vectors indicative of blood outflow from adjacent voxels with respect the voxel of interest.

17. A system for determining a tissue perfusion response using ultrasound, comprising:
 a imaging device for acquiring data comprising voxels using contrast ultrasound; and
 a microprocessor connected to said imaging device for applying a predetermined curve fitting technique to the acquired data to obtain a plurality of fitted curves for a predetermined set of the voxels consisting of adjacent voxels and at least one voxel of interest in the acquired data, said microprocessor determining a time-to-peak parameter value based upon the fitted curves for each of the voxels, said microprocessor excluding any one of the fitted curves corresponding to the adjacent voxel if the time-to-peak parameter value of the adjacent voxel exceeds the time-to-peak parameter value of the voxel of interest to define selected adjacent voxels based upon remaining ones of the fitted curves, said microprocessor determining a local input function by adding the fitted curves from the selected adjacent voxels, said microprocessor determining the tissue perfusion response based upon the local input function and an output function according to the acquired data.

18. The system for determining a tissue perfusion response according to claim 17 wherein the plurality of fitted curves for the adjacent voxels along at least one predetermined direction with respect to the voxel of interest is selected.

19. The system for determining a tissue perfusion response according to claim 17 wherein the output function is based upon the voxel of interest.

20. The system for determining a tissue perfusion response according to claim 17 wherein the output function is based upon a combination of the voxel of interest and excluded ones of the adjacent voxels.

21. The system for determining a tissue perfusion response according to claim 17 wherein the predetermined direction includes a combination of a 3D blood inflow vector and a 3D blood outflow vector with respect the voxel of interest.

22. A method of determining a tissue perfusion response, comprising:
 acquiring time-series data corresponding to a three-dimensional region in a subject in which a contrast agent is injected by using a processing circuitry of a medical diagnosis apparatus, the three-dimensional region including a target position and adjacent positions adjacent to the target position;
 determining time-to-peaks of the target position and the adjacent positions by monitoring voxel values of the time-series data by using the processing circuitry of the medical diagnosis apparatus;
 determining a local input function based on time-series voxel values of a voxel corresponding to at least one of the adjacent positions in which a time-to-peak is smaller than a time-to-peak of the target position by using the processing circuitry of the medical diagnosis apparatus; and
 determining the tissue perfusion response based upon the local input function and an output function by using the processing circuitry of the medical diagnosis apparatus.

* * * * *